US009522104B2

(12) United States Patent
Hattori et al.

(10) Patent No.: US 9,522,104 B2
(45) Date of Patent: Dec. 20, 2016

(54) GELLING AGENT

(71) Applicant: AJINOMOTO CO., INC., Tokyo (JP)

(72) Inventors: Gaku Hattori, Kawasaki (JP); Masahiro Ino, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/447,872

(22) Filed: Jul. 31, 2014

(65) Prior Publication Data

US 2014/0341960 A1    Nov. 20, 2014

Related U.S. Application Data

(63) Continuation of application No. PCT/JP2013/053605, filed on Feb. 7, 2013.

(30) Foreign Application Priority Data

Feb. 8, 2012 (JP) .................. 2012-025338

(51) Int. Cl.

| | |
|---|---|
| *A61K 8/42* | (2006.01) |
| *A61Q 1/06* | (2006.01) |
| *A61Q 15/00* | (2006.01) |
| *C07C 237/22* | (2006.01) |
| *A61K 8/44* | (2006.01) |
| *A61K 8/02* | (2006.01) |
| *A61K 8/37* | (2006.01) |

(52) U.S. Cl.
CPC .............. *A61K 8/42* (2013.01); *A61K 8/0229* (2013.01); *A61K 8/37* (2013.01); *A61K 8/44* (2013.01); *A61K 8/442* (2013.01); *A61Q 1/06* (2013.01); *A61Q 15/00* (2013.01); *C07C 237/22* (2013.01); *A61K 2800/262* (2013.01); *A61K 2800/40* (2013.01)

(58) Field of Classification Search
None
See application file for complete search history.

(56) References Cited

U.S. PATENT DOCUMENTS

| 4,181,527 A | 1/1980 | Toda et al. |
| 5,641,476 A | 6/1997 | Motley |
| 6,423,324 B1 | 7/2002 | Murphy et al. |
| 7,244,419 B2 * | 7/2007 | Yamato ............... A61K 8/0229 424/66 |
| 2002/0159961 A1 | 10/2002 | Yamato et al. |
| 2004/0248812 A1 * | 12/2004 | Hanabusa ............... C09D 5/04 514/18.8 |
| 2005/0208085 A1 | 9/2005 | Yamato et al. |
| 2006/0073177 A1 * | 4/2006 | Yamato ................. A61K 8/042 424/401 |
| 2012/0039972 A1 | 2/2012 | Kobayashi et al. |

FOREIGN PATENT DOCUMENTS

| JP | 53-121615 A | 10/1978 |
| JP | 2002-316971 A | 10/2002 |
| JP | 2005-298635 A | 10/2005 |
| JP | 2009-114161 A | 5/2009 |
| JP | 2010-260824 A | 11/2010 |
| JP | 2010-260825 A | 11/2010 |
| WO | WO 01/97758 A2 | 12/2001 |

OTHER PUBLICATIONS

Brizard et al., Chiral effects in self-assembled fibrillar networks, Top Curr. Chem. 2005, vol. 256, 167-218.*
Okabe et al., Gelation mechanism and microstructure of organogels formed with various types of gelators, J. Poly. Sci.: Part B: Poly, Phy. 2005, vol. 43, p. 3567-3574.*
Zinic et al., in Chiral Gelators Constructed from 11-Aminoundecanoic (AUDA), Lauric and Amino Acid Units. Synthesis, Gelling Properties and Preferred Gelation of Racemates vs. the Pure Enantiomers, Eur. J. Org. Chem. 2004, pp. 4048-4059.*
International Search Report issued May 14, 2013 in PCT/JP2013/053605.
Extended European Search Report issued Sep. 8, 2015 in Patent Application No. 13747265.0.

* cited by examiner

*Primary Examiner* — Bethany Barham
*Assistant Examiner* — Ping Cao
(74) *Attorney, Agent, or Firm* — Oblon, McClelland, Maier & Neustadt, L.L.P.

(57) ABSTRACT

Provided is a gelling agent containing N-acyl acidic amino acid dialkylamide having a DL form ratio (D form/L form (weight/weight)) of 5/95-20/80 or 80/20-95/5, and using the gelling agent, a gel composition, particularly a rod-like gel composition, superior in transparency and strength, and superior in compatibility and spreadability when applied to the skin, hair and the like is provided.

10 Claims, No Drawings

GELLING AGENT

CROSS REFERENCES TO RELATED APPLICATIONS

This application is a continuation of International Patent Application No. PCT/JP2013/053605, filed on Feb. 7, 2013, and claims priority to Japanese Patent Application No. 2012-025338, filed on Feb. 8, 2012, both of which are incorporated herein by reference in their entireties.

BACKGROUND OF THE INVENTION

Field of the Invention

The present invention relates to a gelling agent containing N-acyl acidic amino acid dialkylamide having a particular DL form ratio (component A). In addition, the present invention relates to a gel composition, particularly a rod-like gel composition, containing the N-acyl acidic amino acid dialkylamide (component A), an oily base (component B), and an ester of acylamino acid and dimer diol and/or an ester of acylamino acid and fatty acid and dimer diol (component C).

Discussion of the Background

Heretofore, N-acyl-L-amino acid dialkylamides such as N-lauroyl-L-glutamic acid dibutylamide, N-2-ethyl-hexanoyl-L-glutamic acid dibutylamide and the like have been used as gelling agents for oily bases. While they are known to gel various oily bases, since they have high melting points and show low solubility in oily bases, dissolution thereof requires a high temperature of, for example, 150° C. or above, which is not entirely preferable when substances having poor thermal stability and volatile components are blended.

To solve this problem, a method of combining N-acyl-L-amino acid dialkylamide and sugar fatty acid ester and/or polyol fatty acid ester (patent document 1: JP-A-2009-114161), and a method of using in combination with a particular organic solvent such as behenyl alcohol, octyldodecanol and the like (patent document 2: JP-A-2005-298635) have been proposed. However, they impose a limitation on the formulation design in that a particular component in a particular amount needs to be blended, and further, a gel composition superior in transparency and strength may not be obtained in some cases. As such, they are not necessarily useful solving measures.

On the other hand, gel compositions prepared using N-acyl-L-amino acid dialkylamide sometimes lack texture (e.g., spreadability, compatibility etc.) when applied to the skin or hair. Rod-like cosmetic agents such as rouge and the like are mainly composed of a gelling agent, and an oily base such as wax, waxes, paste oil, liquid oil and the like, and various sensory qualities have been realized by changing the amounts of these. However, use of a large amount of wax and paste oil tends to cause bad sense of use, for example, stickiness, moisture, close adhesiveness and the like. In recent years, therefore, attempts have been made to prepare cosmetic agents with reduced amounts of wax and paste oil.

For example, patent document 3: JP-A-2010-260824 and patent document 4: JP-A-2010-260825 disclose a combined use of N-acyl-L-amino acid dialkylamide and dimer acid ester to afford a superior texture. However, even such use sometimes fails to achieve a sufficient texture.

DOCUMENT LIST

Patent Documents

[patent document 1] JP-A-2009-114161
[patent document 2] JP-A-2005-298635
[patent document 3] JP-A-2010-260824
[patent document 4] JP-A-2010-260825

SUMMARY OF THE INVENTION

Problems to be Solved by the Invention

The problem of the present invention is to provide a gelling agent having an appropriate melting temperature, and provide a gel composition, particularly a rod-like gel composition, which is superior, due to the gelling agent, in transparency and strength, and superior in compatibility and spreadability when applied to the skin, hair and the like.

Means of Solving the Problems

The present inventors have conducted intensive studies in view of the aforementioned problems and found that the above-mentioned problems can be solved by using N-acyl acidic amino acid dialkylamide having a particular DL form ratio as a gelling agent, which resulted in the completion of the present invention.

Accordingly, the present invention includes the following embodiments.

[1] A gelling agent comprising N-acyl acidic amino acid dialkylamide represented by the formula (I):

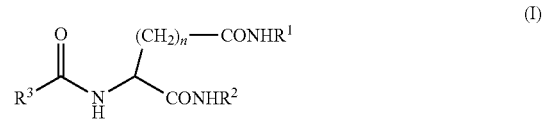

wherein $R^1$ and $R^2$ are each independently a straight chain or branched chain alkyl group having 1-7 carbon atoms, $R^3$ is a straight chain or branched chain alkyl group having 3-15 carbon atoms, and n is 1 or 2, and having a DL form ratio (D form/L form (weight/weight)) of 5/95-20/80 or 80/20-95/5.

[2]-1
The gelling agent of [1], wherein the N-acyl acidic amino acid dialkylamide is N-2-ethyl hexanoyl glutamic acid dibutylamide or N-lauroyl glutamic acid dibutylamide.

[2]-2
The gelling agent of [1], wherein the N-acyl acidic amino acid dialkylamide is a mixture of N-2-ethyl hexanoyl glutamic acid dibutylamide and N-lauroyl glutamic acid dibutylamide.

[3]
The gelling agent of [1] or [2], wherein the DL form ratio (D form/L form (weight/weight)) is 5/95-20/80.

[4]
A gel composition comprising the gelling agent of any one of the above-mentioned [1] to [3] (component A), and an oily base (component B).

[5]
The gel composition of the above-mentioned [4], wherein the oily base (component B) is selected from the group consisting of silicone oil, ester oil, hydrocarbon, higher alcohol, polyvalent alcohol, and fatty acid.

[6]
The gel composition of the above-mentioned [4] or [5], further comprising an ester of acyl amino acid and dimer diol and/or an ester of acylamino acid and fatty acid and dimer diol (component C).

[7]
The gel composition of the above-mentioned [6], wherein the component C is one or more selected from the group consisting of an ester of lauroyl glutamic acid and dimer diol, an ester of lauroyl sarcosine and dimer diol, and bis(lauroyl glutamic acid/lauroyl sarcosine)dimer dilinoleate.
[8]
The gel composition of the above-mentioned [6] or [7], wherein the amount of component A is 0.01-30 wt %, the amount of component C is 0.1-60 wt %, the total of the amounts of component B and component C is 30-99.99 wt %.
[9]
The gel composition of the above-mentioned [4]-[8], which has a shape of a rod.
[10]
The gel composition of the above-mentioned [4]-[9], which is adiaphoretic, chapstick or rouge.

Effect of the Invention

According to the present invention, a gel composition that does not need to be dissolved at a high temperature of 150° C. or above, is superior in transparency and strength, and superior in compatibility and spreadability when applied to the skin, hair and the like can be provided.

DETAILED DESCRIPTION OF THE PREFERRED EMBODIMENTS

The present invention relates to a gelling agent containing N-acyl acidic amino acid dialkylamide (component A) having a particular DL form ratio.

In the present invention, a gelling agent refers to a substance or composition that thickens a liquid, or changes to a jelly state or solid state. In the present invention, it is particularly useful as a gelling agent for oily liquids (oily substrates).

In addition, the present invention relates to a gel composition, particularly a rod-like gel composition, containing the N-acyl acidic amino acid dialkylamide (component A), an oily base (component B), and an ester of acylamino acid and dimer diol and/or an ester of acylamino acid and fatty acid and dimer diol (component C).

N-acyl amino acid dialkylamide (component A)

The N-acyl acidic amino acid dialkylamide (component A) in the present invention is represented by the formula (I).

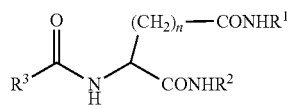

wherein $R^1$ and $R^2$ are each independently a straight chain or branched chain alkyl group having 1-7 carbon atoms. Examples of the straight chain or branched chain alkyl group having 1-7 carbon atoms include methyl group, ethyl group, isopropyl group, propyl group, butyl group, isobutyl group, sec-butyl group, tert-butyl group, pentyl group, sec-pentyl group, tert-pentyl group, isopentyl group, hexyl group, and heptyl group and the like. Since an effective gel strength can be exhibited with a small amount, a straight chain or branched chain alkyl group having 3-5 carbon atoms is preferable, and a butyl group is more preferable. It is more preferable that both $R^1$ and $R^2$ be straight chain or branched chain alkyl groups having 3-5 carbon atoms, and it is further preferable that both $R^1$ and $R^2$ be butyl groups.

In the formula, $R^3$ is a straight chain or branched chain alkyl group having 3-15 carbon atoms. Examples of the straight chain or branched chain alkyl group having 3-15 carbon atoms include propyl group, isopropyl group, butyl group, isobutyl group, sec-butyl group, tert-butyl group, pentyl group, sec-pentyl group, tert-pentyl group, isopentyl group, hexyl group, heptyl group, 1-ethylpentyl group, octyl group, 2-ethylhexyl group, tert-octyl group, nonyl group, isononyl group, decyl group, isodecyl group, undecyl group, dodecyl group, tridecyl group, isotridecyl group, tetradecyl group, and pentadecyl group and the like. Since an effective gel strength can be exhibited with a small amount, a straight chain or branched chain alkyl group having 5-13 carbon atoms is preferable, a straight chain or branched chain alkyl group having 7-11 carbon atoms is more preferable, and a 1-ethyl pentyl group or an undecyl group is most preferable.

n is 1 or 2. When n is 1, component A is N-acyl aspartic acid dialkylamide, and when n is 2, component A is N-acyl glutamic acid dialkylamide. Since an effective gel strength can be exhibited with a small amount, n is preferably 2 (N-acylglutamic acid dialkylamide).

Specific examples of the N-acyl amino acid dialkylamide (component A) include N-hexanoyl glutamic acid diisopropylamide, N-hexanoyl glutamic acid dibutylamide, N-hexanoyl glutamic acid di-sec-butylamide, N-hexanoyl glutamic acid diisobutylamide, N-octanoyl glutamic acid diisopropylamide, N-octanoyl glutamic acid dibutylamide, N-octanoyl glutamic acid di-sec-butylamide, N-octanoyl glutamic acid diisobutylamide, N-2-ethyl hexanoyl glutamic acid dimethylamide, N-2-ethylhexanoyl glutamic acid diethylamide, N-2-ethylhexanoyl glutamic acid dipropylamide, N-2-ethylhexanoyl glutamic acid diisopropylamide, N-2-ethylhexanoyl glutamic acid dibutylamide, N-2-ethylhexanoyl glutamic acid di-sec-butylamide, N-2-ethylhexanoyl glutamic acid diisobutylamide, N-2-ethylhexanoyl glutamic acid dipentylamide, N-2-ethylhexanoyl glutamic acid dihexylamide, N-decanoyl glutamic acid diisopropylamide, N-decanoyl glutamic acid dibutylamide, N-decanoyl glutamic acid di-sec-butylamide, N-decanoyl glutamic acid diisobutylamide, N-lauroyl glutamic acid dimethylamide, N-lauroyl glutamic acid diethylamide, N-lauroyl glutamic acid dipropylamide, N-lauroyl glutamic acid diisopropylamide, N-lauroyl glutamic acid dibutylamide, N-lauroyl glutamic acid di-sec-butylamide, N-lauroyl glutamic acid diisobutylamide, N-lauroyl glutamic acid dipentylamide, N-lauroyl glutamic acid dihexylamide, N-palmitoyl glutamic acid diisopropylamide, N-palmitoyl glutamic acid dibutylamide, N-palmitoyl glutamic acid di-sec-butylamide, N-palmitoyl glutamic acid diisobutylamide, N-myristoyl glutamic acid diisopropylamide, N-myristoyl glutamic acid dibutylamide, N-myristoyl glutamic acid di-sec-butylamide, N-myristoyl glutamic acid diisobutylamide, N-2-ethylhexanoyl aspartic acid diisopropylamide, N-2-ethylhexanoyl aspartic acid dibutylamide, N-2-ethylhexanoyl aspartic acid di-sec-butylamide, N-2-ethylhexanoyl aspartic acid diisobutylamide, N-lauroyl aspartic acid diisopropylamide, N-lauroyl aspartic acid dibutylamide, N-lauroyl aspartic acid di-sec-butylamide, and N-lauroyl aspartic acid diisobutylamide can be mentioned, preferably, N-2-ethylhexanoyl glutamic acid diisopropylamide, N-2-ethylhexanoyl glutamic acid dibutylamide, N-2-ethylhexanoyl glutamic acid di-sec-butylamide, N-2-ethylhexanoyl glutamic acid diisobutylamide, N-lauroyl glutamic acid diisopropylamide, N-lauroyl glutamic acid dibutylamide, N-lauroyl glutamic acid di-sec-butylamide and N-lauroyl glutamic acid diisobutylamide. More preferred are N-2-ethylhexanoyl glutamic acid dibutylamide and N-lauroyl glutamic acid dibutylamide. As component (A), one or more kinds of N-acyl amino acid dialkylamides can also be used.

The N-acyl acidic amino acid dialkylamide represented by the formula (I) has an asymmetric carbon on an amino acid residue and, and a DL form ratio (D form/L form (weight/weight)) of 5/95-20/80 or 80/20-95/5 based on such asymmetric carbon. It is preferably 5/95-15/85 or 85/15-95/5, more preferably 7/93-13/87 or 87/13-93/7. It is further preferably 5/95-20/80, still more preferably 5/95-15/85, and particularly preferably 7/93-13/87. As regards an asymmetric carbon in a molecule other than these, stereoisomers such as optical isomer, diastereomer and the like, a mixture of any stereoisomers, or racemate may also be used.

[Oily Base (Component B)]

The N-acyl amino acid dialkylamide (component A) in the present invention is dissolved in an oily base (component B) by heating and cooled to room temperature, whereby a gel composition can be prepared. Specific examples of the oily base (component B) include silicone oil such as methyl polysiloxane, polymethyl polysiloxane, polyoxyethylene/methylpolysiloxane copolymer, polyoxypropylene/methylpolysiloxane copolymer, poly(oxyethylene, oxypropylene)/methylpolysiloxane copolymer, stearoxy methylpolysiloxane, stearoxy trimethylsilane, methylhydrogenpolysiloxane, octamethyl polysiloxane, decamethyl polysiloxane, decamethyl cyclopentasiloxane, octamethyl cyclotetrasiloxane, tetrahydrotetramethyl cyclotetrasiloxane, methylcyclopolysiloxane, cyclopentasiloxane, dodecamethylcyclohexasiloxane, methylphenylpolysiloxane, trimethylsiloxy-silicic acid, aminoethyl aminopropyl siloxane/dimethylsiloxane, silanol-denatured polysiloxane, alkoxy-denatured polysiloxane, fatty acid-denatured polysiloxane, fluorine-denatured polysiloxane, epoxy-denatured polysiloxane, alkoxy-denatured polysiloxane perfluoropolyether, polyvinyl acetate dimethylpolysiloxane and the like; ester oil such as myristyl myristate, hexyl laurate, decyl oleate, isopropyl myristate, hexyldecyl dimethyl octanoate, glycerol monostearate, glyceryl tri-2-ethylhexanoate, diethyl phthalate, ethylene glycol monostearate, octyl oxystearate, benzoic acid alkyl ester and the like; hydrocarbon such as liquid paraffin, polyisobutene, petrolatum, squalane and the like; higher alcohol such as cetyl alcohol, isostearyl alcohol, lauryl alcohol, hexadecyl alcohol, octyldodecanol and the like; fatty acid such as isostearic acid, undecylenoic acid, oleic acid and the like; wax such as lanolin, hydrogenated lanolin, carnauba wax and the like; fats and oils such as mink oil, cacao oil, coconut oil, palm kernel oil, camellia oil, sesame oil, castor oil, olive oil and the like; ethylene/α-olefin/co-oligomer and the like. Silicone oil, ester oil, hydrocarbon, higher alcohol, and fatty acid are preferable, and silicone oil, ester oil, hydrocarbon, and higher alcohol are more preferable.

[Ester of Acylamino Acid and Dimer Diol and/or Ester of Acylamino Acid and Fatty Acid and Dimer Diol (Component C)]

When ester of acylamino acid and dimer diol and/or ester of acylamino acid and fatty acid and dimer diol (component C) is added to the gel composition of the present invention, a gel composition further superior in compatibility and spreadability, and free of stickiness can be obtained.

Dimer diol has a hydroxyl group at the position of carboxyl group moiety of a dimer acid. For example, dimer acid or a lower alcohol ester thereof is hydrogenated preferably in the presence of a catalyst to convert carboxyl group moiety of dimer acid to a hydroxyl group. Dimer acid is a two-base acid obtained by an intermolecular polymerization reaction of unsaturated fatty acids. Generally, a compound obtained by dimerizing unsaturated fatty acid having 11-22 carbon atoms with a clay catalyst and the like is preferable. Preferable examples of the unsaturated fatty acid to be dimerized include myristoleic acid, palmitoleic acid, oleic acid, elaidic acid, vaccenic acid, gadoleic acid, erucic acid, linoleic acid, linolenic acid, arachidonic acid and the like. Dimer acid can be a saturated aliphatic dibasic acid by reducing a double bond present in the dimer acid residue by hydrogenation reduction. Examples of the lower alcohol ester of dimer acid include alcohol-derived ester having 1-6, preferably 2-4, carbon atoms.

Dimer diol contains diol generally having 22-44, preferably 24-40, more preferably about 36, carbon atoms, as a main component. Industrially-obtained dimer diol may sometimes contain, depending on the purification level of dimer acid and lower alcohol ester thereof to be used as starting materials, for example, trimer triol, monomer alcohol and ether compound. In general, one having a dimer diol content of 70-100 wt %, one having a dimer diol content of 90-100 wt % with further purification and the like are available, and these can be used. In the present invention, any of them can be used. As for dimer diol, one derived from animal fats and oils and one derived from plant fats and oils are available, and one derived from plant fats and oils is desirable.

As the acyl group of the acylamino acid moiety of component C, alkanoyl group is preferable, which generally has 2-26, preferably 2-22, more preferably 12-18, carbon atoms. Examples thereof include those derived from straight chain saturated fatty acid such as acetic acid, butanoic acid, hexanoic acid, octanoic acid, lauric acid, myristic acid, palmitic acid, stearic acid, behenic acid and the like, straight chain unsaturated fatty acid such as oleic acid, linoleic acid, linolenic acid, elaidic acid and the like, branched fatty acid such as isobutanoic acid, isopentanoic acid, isohexanoic acid, 2-ethylhexanoic acid, 2-hexyldecanoic acid, isostearic acid and the like, and the like.

While the kind of amino acid of the acylamino acid moiety of component C is not particularly limited, neutral amino acid and acidic amino acid are preferable. Preferable examples of amino acid particularly include glycine, alanine, threonine, β-alanine, sarcosine, N-methyl-β-alanine, aminobutyric acid, glutamic acid, and aspartic acid.

As the fatty acid constituting the part of ester relating to component C, which is derived from fatty acid, fatty acid having 2-26 carbon atoms is preferable. Examples thereof include straight chain saturated fatty acid such as acetic acid, butanoic acid, hexanoic acid, octanoic acid, lauric acid, myristic acid, palmitic acid, stearic acid, behenic acid and the like, straight chain unsaturated fatty acid such as oleic acid, linoleic acid, linolenic acid, elaidic acid and the like, and branched fatty acid such as isobutanoic acid, isopentanoic acid, isohexanoic acid, 2-ethylhexanoic acid, 2-hexyldecanoic acid, isostearic acid and the like.

The ester of acylamino acid and dimer diol for component C can be obtained by esterification or transesterification of, for example, dimer diol with acylamino acid such as acyl neutral amino acid, acyl acidic amino acid and the like mentioned above. The conditions of esterification reaction are not particularly limited. In general, a conventionally used method is employed. For example, the reaction can be performed at 50° C.-200° C. using paratoluene sulfonic acid, sulfuric acid, hydrochloric acid, methanesulfonic acid, hydrogen fluoride and the like as a catalyst and benzene, toluene, xylene and the like as a solvent. Alternatively, the reaction can be performed at 100-200° C. without catalyst and without solvent. For transesterification, an alkali catalyst such as sodium hydroxide, potassium hydroxide, potassium carbonate and the like, metal alkoxide such as sodium methoxide and the like, and the like can be used as a catalyst. As for the order of the reaction steps of acylation reaction and ester reaction, esterification of amino acid may be performed as the first step, and acylation may be performed as the second step.

Specific examples of the ester of acylamino acid and dimer diol and/or ester of acylamino acid and fatty acid and dimer diol (component C) include ester of lauroyl glutamic acid and isostearic acid and dimer diol, ester of lauroylsarcosine and isostearic acid and dimer diol, ester of lauroyl glutamic acid and dimer diol, ester of lauroylsarcosine and dimer diol, and ester of bis(lauroyl glutamic acid/lauroylsarcosine)dimer dilinoleate. More preferred are ester of lauroyl glutamic acid and dimer diol, ester of lauroylsarcosine and dimer diol, and bis(lauroyl glutamic acid/lauroylsarcosine)dimer dilinoleate, and further preferred is bis(lauroyl glutamic acid/lauroylsarcosine)dimer dilinoleate.

While the shape of the gel composition of the present invention is not particularly limited, it is, for example, paste, cream, particle, solid, rod, sphere, sheet and the like. When the gel composition of the present invention forms a rod, a product superior in transparency and strength, and superior in compatibility and spreadability when applied to the skin, hair and the like can be obtained.

The amount of N-acyl amino acid dialkylamide (component A) in the gel composition of the present invention is not particularly limited as long as the oily base can gel. Since a gel composition superior in gel strength and spreadability is obtained, the lower limit of the amount (wt %) of the gelling agent relative to the whole gel composition is preferably 0.01 wt %, more preferably 0.1 wt %, further preferably 0.3 wt %, still more preferably 0.5 wt %. Since a gel composition superior in transparency and compatibility can be obtained, the upper limit of the amount (wt %) of the gelling agent relative to the whole gel composition is preferably 30 wt %, more preferably 20 wt %, further preferably 15 wt %, still more preferably 12 wt %, most preferably 10 wt %.

The amount of oily base (component B) to be used for the gel composition of the present invention is not particularly limited as long as gelling proceeds. Since a gel network is formed and maintained, the lower limit of the amount (wt %) of the oily base relative to the whole gel composition is preferably 30 wt %, more preferably 40 wt %, further preferably 50 wt %, still more preferably 60 wt %, most preferably 70 wt %. Since a gel can be formed efficiently, the upper limit of the amount (wt %) of the oily base relative to the whole gel composition is preferably 99.99%, more preferably 99.9%, further preferably 99.5%.

When used in combination with component C, the total weight of component B and component C is adjusted to 30 wt %-99.99 wt %. Since a gel network is formed and maintained, the total weight of component B and component C is preferably 30 wt %, more preferably 40 wt %, further preferably 50 wt %, still more preferably 60 wt %, most preferably 70 wt %. Since a gel can be formed efficiently, the upper limit of the amount (wt %) of the oily base relative to the whole gel composition is preferably 99.99%, more preferably 99.9%, further preferably 99.5%.

From the aspect of the sense of use, the upper limit (mass ratio) of the amount of component C in the gel composition of the present invention is preferably 60 wt %, more preferably 40 wt %, further preferably 20 wt %, still more preferably 15 wt %. On the other hand, from the aspect of the sense of use, the lower limit (mass ratio) is preferably 0.1 wt %, more preferably 0.2 wt %, further preferably 0.3 wt %, particularly preferably 0.5 wt %.

When the shape of the gel composition is rod, the amount of component A is 0.01-30 wt %, and the amount of component C is 0.1-60 wt %. The total amount of component B and component C is 30-99.99 wt %.

The gel composition of the present invention can contain components generally used for cosmetic agents such as various chelating agents, antiperspirant active ingredient, surfactant, various additives, various powders and the like within the range where the effect of the present invention is not inhibited. In a narrow sense, a gel composition means a composition composed only of a gelling agent and an oily substrate and, in a wide sense, it also means a cosmetic agent, aromatic and a quasi-drug as a final product further containing additives.

While various chelating agents are not particularly limited, preferable examples include a chelator selected from the group consisting of triethylenetetramine, 2-thenoyltrifluoroacetone, thioglycolic acid, tartaric acid, succinic acid, 8-quinolinol, pyridine-2,6-dicarboxylic acid, pyridine, 1,10-phenanthroline, lactic acid, 8-hydroxyquinoline-5-sulfonic acid, glycine, 2,2'-pyridylethylenediamine, aurintricarboxylic acid, xylenol orange, 5-sulfosalicyl acid, salicylic acid, pyrocatechol-3,5-disulfonate, 4,5-dihydroxybenzene-1,3-disulfonic acid, 1,2-diaminocyclohexane-N,N,N',N'-tetraacetic acid, citric acid, oxalate, nitrilotriacetic acid, ethylenediamine-N,N,N',N'-tetraacetic acid, acetylacetone, and salts thereof and a mixture thereof and the like.

Examples of the antiperspirant active ingredient include one kind selected from the group consisting of chlorohydroxyaluminum, aluminum chloride, chlorohydroxyaluminum allantoinate, aluminum sulfate, zinc oxide, zinc paraphenolsulfonate, and zirconium aluminum complex produced by reacting zirconylchloride with aluminum hydroxide and aluminumchlorohydroxide, and a mixture thereof. As used herein, the antiperspirant active ingredient refers to a component that suppresses sweating by causing strong adstriction of the skin.

Examples of the surfactant include anionic surfactant such as N-long chain acyl amino acid salt (N-long chain acyl acidic amino acid salt, N-long chain acyl neutral amino acid salt and the like), N-long chain fatty acid acyl-N-methyltaurine salt, alkylsulfate and alkylene oxide adduct thereof, fatty acid amide ether sulfate, metal salt or weak base salt of fatty acid, sulfosuccinic acid-based surfactant, alkyl phosphate and alkylene oxide adduct thereof, alkylethercarboxylic acid, and the like; non-ionic surfactant such as ether type surfactant (glycerol ester and alkylene oxide adduct thereof and the like), ester type surfactant (glycerol ether and alkylene oxide adduct thereof and the like), etherester type surfactant (sorbitan ester and alkylene oxide adduct thereof and the like), ester type surfactant (polyoxyalkylene fatty acid ester, glycerol ester, fatty acid polyglycerol ester, sorbitan ester, sucrose fatty acid ester and the like), nitrogen-containing non-ionic surfactant (alkyl glucosides, hydrogenated castor oil pyroglutamic acid diester and ethylene oxide adduct thereof, fatty acid alkanol amide and the like); cationic surfactant such as aliphatic amine salt (alkyl ammonium chloride, dialkyl ammonium chloride and the like), aromatic quaternary ammonium salt (quaternary ammonium salt thereof, benzalkonium salt thereof and the like), fatty acid acyl arginine ester, and the like; and amphoteric surfactant (betaine type surfactant (carboxybetaine and the like), aminocarboxylic acid type surfactant, imidazoline type surfactant and the like, and the like.

Examples of the various additives include amino acids such as glycine, alanine, serine, threonine, arginine, glutamic acid, aspartic acid, isoleucine, leucine, valine and the like; polyvalent alcohol such as glycerol, ethylene glycol, 1,3-butylene glycol, propylene glycol, isoprene glycol and the like; water-soluble polymer such as polyglutamic acid, polyamino acid containing polyaspartic acid and a salt thereof, polyethylene glycol, gum arabic, alginates, xanthan gum, hyaluronic acid, hyaluronic acid salt, chitin, chitosan, water-soluble chitin, carboxyvinyl polymer, carboxymethyl cellulose, hydroxyethyl cellulose, hydroxypropyl trimethylammonium chloride, polychlorodimethylmethylene piperidium, polyvinylpyrrolidone derivative quaternary ammonium, cationized protein, collagen degradation products and a derivative thereof, acylation protein, polyglycerol, and the like; sugar alcohol such as mannitol and alkylene oxide adduct thereof; lower alcohol such as ethanol, propanol and the like, animals and plants extract, nucleic acid, vitamin, enzyme, anti-inflammatory agent, antimicrobial agent, preservative, antioxidant, UV absorber, chelating agent, adiaphoretic, pigment, dye, oxidation dye, organic and inorganic powder, pH adjuster, pearl agent, wetting agent and the like.

Examples of the various powders include resin powder such as nylon beads, silicone beads and the like, nylon powder, metal fatty acid soap, yellow iron oxide, red iron oxide, black iron oxide, chrome oxide, cobalt oxide, carbon black, ultramarine blue, iron blue, zinc oxide, titanium oxide, zirconium oxide, silicon oxide, aluminum oxide, cerium oxide, micatitanium, boron nitride, barium sulfate, calcium carbonate, magnesium carbonate, aluminum silicate, magnesium silicate, silicon carbide, dye, lake, sericite, mica, talc, kaolin, plate-shaped barium sulfate, butterfly-shaped barium sulfate, titanium oxide fine particles, zinc oxide fine particles, iron oxide fine particles, acylamino acid such as acyllysine, acyl glutamic acid, acyl arginine, acyl glycine and the like, and the like can be mentioned, which may be further subjected to a surface treatment such as silicone treatment, fluorine compound treatment, silane coupling agent treatment, silane treatment organic titanate treatment, acylation lysine treatment, fatty acid treatment, metal soap treatment, oil treatment, amino acid treatment and the like.

The present invention further relates' to a cosmetic agent or a quasi-drug, which contains the gel composition of the present invention, or which is the gel composition of the present invention itself, irrespective of the shape and size. Specific examples of the cosmetic agent of the present invention include adiaphoretic, facial cleanser, cleansing gel, skin milk, massage cream, cold cream, moisture gel, facial mask, aftershave gel, foundation, chapstick, rouge, cheek, mascara, shampoo, rinse, hair-growth drug, hair treatment, hair conditioner, tic, set lotion, hair cream, hair wax, hair mousse, perm solution, hair dye, hair coloring, hair manicure, sunscreen oil, hand soap, aromatic, fomentation and the like, which is preferably adiaphoretic, chapstick or rouge.

EXAMPLES

The present invention is explained in more detail in the following by referring to Examples, which are not to be construed as limitative.

Synthetic Example 1

N-2-ethylhexanoyl-L-glutamic acid dibutylamide synthesis method: L-sodium glutamate monohydrate (110 g) was dissolved in water (140 g) and 25% aqueous sodium hydroxide solution (84 g), and the mixture was cooled to 10° C. Acetone (110 g) was added, and 2-ethylhexanoyl chloride (87 g) and 25% aqueous sodium hydroxide solution (84 g) were added dropwise. The acylation reaction mixture was diluted with water (100 g), and neutralized with 75% sulfuric acid (80 g) to separate oil. The aqueous layer was removed, and the oil layer was concentrated under reduced pressure to give an oily substance. The oily substance was dissolved in methanol (742 g), 75% sulfuric acid (7.9 g) was added and the mixture was refluxed for 9 hr. The reaction mixture was allowed to cool to 35° C., neutralized with n-butylamine (8.8 g) and methanol was evaporated to give an oily substance. To the oily substance were added toluene (643 g) and n-butylamine (271 g), and the mixture was stirred with heating at 90° C. for 10 hr. Thereto were added warm water (506 g) and 75% sulfuric acid (165 g) to allow for oil separation and the aqueous layer was removed. To the oil layer was added warm water (1200 g), the solvent was removed under normal pressure to give a white solid slurry liquid. The solid was filtered, recrystallized from methanol-acetone mixed solvent, filtered, and dried in vacuo at 50° C. to give N-2-ethylhexanoyl-L-glutamic acid dibutylamide (50 g).

NMR: $^1$H-NMR peak (CDCl$_3$) δ:0.85-0.95 (m, 12H), 1.25-1.62 (m, 16H), 1.98-2.10 (m, 3H), 2.26-2.33 (m, 1H), 2.42-2.50 (m, 1H), 3.22-3.29 (m, 4H), 4.30-4.36 (m, 1H), 5.97 (br, 1H), 6.91 (br, 1H), 7.12 (br, 1H)

melting point: 200° C.

DL form ratio (D form/L form (weight/weight)): 0/100

Synthetic Example 2

N-2-ethylhexanoyl-DL-glutamic acid dibutylamide synthesis method: DL-glutamic acid (63 g) was dissolved in water (130 g) and 25% aqueous sodium hydroxide solution (126 g), and the mixture was cooled to 10° C. Isopropyl alcohol (63 g) was added, and 2-ethylhexanoyl chloride (64 g) and 25% aqueous sodium hydroxide solution (74 g) were added dropwise. The acylation reaction mixture was neutralized with 75% sulfuric acid (56 g) to separate oil. The aqueous layer was removed, and the oil layer was concentrated under reduced pressure to give an oily substance. The oily substance was dissolved in n-butanol (221 g), 98% sulfuric acid (7.7 g) was added and the mixture was refluxed for 8 hr. The reaction mixture was concentrated under reduced pressure to give an oily substance. To the oily substance was added n-butylamine (180 g) and the mixture was stirred at with heating at 90° C. for 8 hr. The reaction mixture was concentrated under reduced pressure to give an oily substance, and water (300 g) was added. The mixture was neutralized with 75% sulfuric acid to allow for oil separation and the aqueous layer was removed. The oil layer was concentrated under reduced pressure to give a white solid slurry liquid. The solid was filtered and dried in vacuo at 50° C. to give N-2-ethylhexanoyl-DL-glutamic acid dibutylamide (105 g).

NMR: $^1$H-NMR peak (CDCl$_3$) δ:0.85-0.95 (m, 12H), 1.25-1.62 (m, 16H), 1.98-2.10 (m, 3H), 2.26-2.33 (m, 1H), 2.42-2.50 (m, 1H), 3.22-3.29 (m, 4H), 4.30-4.36 (m, 1H), 5.97 (br, 1H), 6.91 (br, 1H), 7.12 (br, 1H)

melting point: 175° C.

DL form ratio (D form/L form (weight/weight)): 50/50

Synthetic Example 3

N-lauroyl-L-glutamic acid dibutylamide synthesis synthesis method: L-sodium glutamate monohydrate (110 g) was dissolved in water (140 g) and 25% aqueous sodium hydroxide solution (84 g), and the mixture was cooled to 10° C. Acetone (110 g) was added, and lauroyl chloride (116 g) and 25% aqueous sodium hydroxide solution (80 g) were added dropwise. The acylation reaction mixture was diluted with water (100 g), and neutralized with 75% sulfuric acid (80 g) to separate oil. The aqueous layer was removed, and the oil layer was concentrated under reduced pressure to give an oily substance. The oily substance was dissolved in methanol (742 g), 75% sulfuric acid (7.9 g) was added and the mixture was refluxed for 9 hr. The reaction mixture was allowed to cool to 35° C., neutralized with n-butylamine (8.8 g) and methanol was evaporated to give an oily substance. To the oily substance were added toluene (643 g) and n-butylamine (271 g), and the mixture was stirred at 90° C. for 10 hr with heating. Thereto were added warm water (506 g) and 75% sulfuric acid (165 g) to allow for oil separation and the aqueous layer was removed. To the oil layer was added warm water (1200 g), the solvent was removed under normal pressure to give a white solid slurry liquid. The solid was filtered, recrystallized from methanol, filtered, and dried in vacuo at 50° C. to give N-lauroyl-L-glutamic acid dibutylamide (58 g).

NMR: $^1$H-NMR peak (CDCl$_3$) δ:0.86-0.95 (m, 9H), 1.25-1.66 (m, 26H), 1.92-2.10 (m, 2H), 2.20-2.32 (m, 3H), 2.38-2.48 (m, 1H), 3.22-3.28 (m, 4H), 4.32-4.36 (m, 1H), 6.03 (br, 1H), 6.82 (br, 1H), 7.00 (br, 1H)

melting point: 166° C.

DL form ratio (D form/L form (weight/weight)): 0/100

Synthetic Example 4

N-lauroyl-DL-glutamic acid dibutylamide synthesis synthesis method: DL-glutamic acid (57 g) was dissolved in water (120 g) and 25% aqueous sodium hydroxide solution (108 g), and the mixture was cooled to 10° C. Isopropyl alcohol (57 g) was added, and lauroyl chloride (79 g) and 25% aqueous sodium hydroxide solution (71 g) were added dropwise. The acylation reaction mixture was neutralized with 75% sulfuric acid (50 g) to precipitate white solid, which was filtered and washed with water. The solid was dissolved in n-butanol (200 g), 98% sulfuric acid (7.4 g) was added and the mixture was refluxed for 8 hr. The reaction mixture was concentrated under reduced pressure to give an oily substance. To the oily substance was added n-butylamine (164 g) and the mixture was stirred with heating at 90° C. for 8 hr. The reaction mixture was concentrated under reduced pressure to give an oily substance and water (300 g) was added. The mixture was neutralized with 75% sulfuric acid to allow for oil separation and the aqueous layer was removed. The oil layer was concentrated under reduced pressure to give a white solid slurry liquid. The solid was filtered and dried in vacuo at 50° C. to give N-lauroyl-DL-glutamic acid dibutylamide (98 g).

NMR: $^1$H-NMR peak (CDCl$_3$) δ: 0.86-0.95 (m, 9H), 1.25-1.66 (m, 26H), 1.92-2.10 (m, 2H), 2.20-2.32 (m, 3H), 2.38-2.48 (m, 1H), 3.22-3.28 (m, 4H), 4.32-4.36 (m, 1H), 6.03 (br, 1H), 6.82 (br, 1H), 7.00 (br, 1H)

melting point: 142° C.

DL form ratio (D form/L form (weight/weight)): 50/50

DL comparison was measured by chiral HPLC (manufactured by SHIMADZU CORPORATION, HPLC Class-LC10 series) under the following conditions.
column: CHIRALPAK AS (manufactured by Daicel)
column temperature: 40° C.
detection: 254 nm (UV)
eluent: hexane/isopropyl alcohol 96/4
flow rate: 1.0 mL/min
NMR was measured using (manufactured by BRUKER, AVANCE 400) and the peak of tetramethylsilane as 0 ppm.

<DL Form Ratio and Function Evaluation of N-2-Ethylhexanoyl Glutamic Acid Dibutylamide>

[Melting Temperature]

N-2-ethylhexanoylglutamic acid dibutylamide having a DL form ratio (D form/L form (weight/weight)) of 50/50, 30/70, 10/90, 0/100 was added to four kinds of component B (mineral oil, isopropyl myristate, triethylhexanoin, cyclopentasiloxane/octyldodecanol (80/20 mixture)) at 1 wt %, and the mixture was placed in a 50 mL sample tube bottle, maintained and stirred for 20 min in an oil bath at 90° C. When the mixture was not dissolved, the temperature of the oil bath was increased by 5° C., and the same procedure was repeated, and the temperature at which each N-2-ethylhexanoyl glutamic acid dibutylamide was completely dissolved was measured as a melting temperature (t). Using the melting temperature (t$_0$) of N-2-ethylhexanoyl glutamic acid dibutylamide having a DL ratio of 0/100, the results were evaluated according to the following criteria.

N-2-ethylhexanoyl glutamic acid dibutylamide having a DL ratio of 30/70, 10/90 was prepared by appropriately mixing N-2-ethylhexanoyl glutamic acid dibutylamide of Synthetic Example 1 and Synthetic Example 2. The same applies to the following Examples.

⊙: t-t$_0$ 25° C. or above
○: t-t$_0$ 15° C. or above and less than 25° C.
Δ: t-t$_0$ 5° C. or above and less than 15° C.
x: t-t$_0$ less than 5° C.

[Gel Strength]

To four kinds of component B same as above was added N-2-ethylhexanoyl glutamic acid dibutylamide same as above at 1 wt %, and the mixture was dissolved by heating in an oil bath, and allowed to cool in a room at room temperature 25° C. for 24 hr to give a gel composition. The gel strength (G) of the obtained gel composition was measured by rheometer (FUDOH RHEOMETER NRM-2010-J-CW), and the results were evaluated according to the following criteria and using the gel strength (G$_0$) of N-2-ethylhexanoyl glutamic acid dibutylamide having a DL ratio of 0/100.

Evaluation followed the criteria below. Adapter was for plume, viscoelasticity, 10ϕ, and the sample table rate was 6 cm/min.

⊙: G/G$_0$ exceeding 1.0
○: G/G$_0$ exceeding 0.5 not more than 1.0
Δ: G/G$_0$ exceeding 0.3 and not more than 0.5
x: G/G$_0$ not more than 0.3

[Permeation Rate]

The permeation rate (T) of the obtained above gel composition was measured by spectrophotometer (V-750: manufactured by JASCO Corporation, wavelength 520 nm, optical path length 1 cm), and evaluated using the permeation rate of N-2-ethylhexanoylglutamic acid dibutylamide having a DL ratio of 0/100 as (T$_0$) and according to the following criteria.

⊙: T/T$_0$ exceeding 1.0
○: T/T$_0$ exceeding 0.6 and not more than 1.0
Δ: T/T$_0$ exceeding 0.4 and not more than 0.6
x: T/T$_0$ not more than 0.4

[Spreadability, Compatibility]

The gel compositions obtained above was applied to the skin and compatibility and spreadability were evaluated by 4 professional panelists according to the following criteria.

spreadability on the skin (evaluated with 4 points as full mark)
4: very good spreadability
3: good spreadability
2: bad spreadability
1: very bad spreadability compatibility with skin (evaluated with 4 points as full mark)
4: very good compatibility with skin
3: good compatibility with skin
2: bad compatibility with skin
1: very bad compatibility with skin Average points of evaluation of not less than 3.5 is marked with ⊙, not less than 2.5 and less than 3.5 is marked with ○, not less than 1.5 and less than 2.5 is marked with Δ, less than 1.5 is marked with x. The evaluation results are also shown in Table 1.

[Comprehensive Evaluation]

Comprehensive evaluation was calculated with ⊙ as 3 points, ○ as 2 points, Δ as 1 point, x as 0 point.

Component B used for the experiment was as follows.
mineral oil: manufactured by Muramatsu petroleum, MORESCO WHITE P-55
isopropyl myristate: manufactured by Kokyu Alcohol Kogyo Co., Ltd., IPM-R
triethylhexanoin: manufactured by Kokyu Alcohol Kogyo Co., Ltd., TOG
cyclopentasiloxane: manufactured by TORAY•Dow Corning Corporation, SH245
octyldodecanol: manufactured by Kokyu Alcohol Kogyo Co., Ltd., RISONOL20SP

TABLE 1

| | DL form ratio of N-2-ethylhexanoyl glutamic acid dibutylamide | component B | comprehensive evaluation | melting temperature (° C.) | melting temperature | gel strength | permeation rate | compatibility | spreadability |
|---|---|---|---|---|---|---|---|---|---|
| Ex. 1 | 10/90 | mineral oil | 12 | 150 | ○ | ○ | ○ | ◉ | ◉ |
| Ex. 2 | | isopropyl myristate | 12 | 130 | ○ | ○ | ○ | ◉ | ◉ |
| Ex. 3 | | triethylhexanoin | 12 | 130 | ○ | ○ | ○ | ◉ | ◉ |
| Ex. 4 | | cyclopentasiloxane/ octyldodecanol 80/20 | 12 | 130 | ○ | ○ | ○ | ◉ | ◉ |
| Comp. Ex. 1 | 50/50 | mineral oil | 4 | 140 | ◉ | X | X | Δ | X |
| Comp. Ex. 2 | | isopropyl myristate | 5 | 120 | ◉ | X | X | ○ | X |
| Comp. Ex. 3 | | triethylhexanoin | 6 | 120 | ◉ | Δ | X | ○ | X |
| Comp. Ex. 4 | | cyclopentasiloxane/ octyldodecanol 80/20 | 6 | 120 | ◉ | Δ | Δ | Δ | X |
| Comp. Ex. 5 | 30/70 | mineral oil | 7 | 145 | ○ | ○ | Δ | ○ | X |
| Comp. Ex. 6 | | isopropyl myristate | 7 | 125 | ○ | Δ | Δ | ◉ | X |
| Comp. Ex. 7 | | triethylhexanoin | 7 | 125 | ○ | Δ | Δ | ◉ | X |
| Comp. Ex. 8 | | cyclopentasiloxane/ octyldodecanol 80/20 | 7 | 125 | ○ | ○ | Δ | ○ | X |
| Comp. Ex. 9 | 0/100 | mineral oil | 6 | 165 | X | ○ | ○ | X | ○ |
| Comp. Ex. 10 | | isopropyl myristate | 7 | 145 | X | ○ | ○ | X | ◉ |
| Comp. Ex. 11 | | triethylhexanoin | 7 | 145 | X | ○ | ○ | X | ◉ |
| Comp. Ex. 12 | | cyclopentasiloxane/ | 6 | 145 | X | ○ | ○ | X | ○ |

From Table 1, it is clear that the melting temperature of N-2-ethylhexanoyl glutamic acid dibutylamide having a DL form ratio of 10/90 is about 15° C. lower than that of N-2-ethylhexanoyl glutamic acid dibutylamide having a DL form ratio of 0/100. In addition, the gel composition prepared from N-2-ethylhexanoyl glutamic acid dibutylamide having a DL form ratio of 10/90 showed desirable property in all of the gel strength, permeation rate, compatibility, and spreadability, and the comprehensive evaluation was higher than other DL ratios.

<DL Form Ratio and Function Evaluation of N-Lauroyl Glutamic Acid Dibutylamide>

In the same manner as above except that N-2-ethylhexanoyl glutamic acid dibutylamide was changed to N-lauroyl glutamic acid dibutylamide, the melting temperature, gel strength, permeation rate, compatibility, and spreadability were measured and evaluated. (2 wt % N-lauroyl glutamic acid dibutylamide was added only to cyclopentadecane/octyldodecanol)

From Table 2, it is clear that the melting temperature of N-lauroyl glutamic acid dibutylamide having a DL form ratio of 10/90 is about 15° C. lower than that of N-lauroyl glutamic acid dibutylamide having a DL form ratio of 0/100. In addition, the gel composition prepared from N-lauroyl glutamic acid dibutylamide having a DL form ratio of 10/90 showed desirable property in all of the gel strength, permeation rate, compatibility, and spreadability, and the comprehensive evaluation was higher than other DL ratios.

<Evaluation of Chapstick (Rod Composition)>
[Spreadability, Compatibility, Stickiness]

The starting materials shown in the following Table 3 were dissolved by heating in an oil bath at 140° C., and allowed to cool in an exclusive container for 24 hr, and in a room at room temperature 25° C., whereby chapstick was prepared. Since the chapstick of Comparative Example 27 could not be prepared at 140° C., an oil bath was used at 150° C.

The chapsticks obtained in Table 3 were applied to the skin and evaluated for 3 items of (1) spreadability, (2) compat-

TABLE 2

| | DL form ratio of N-lauroyl glutamic acid dibutylamide | component B | comprehensive evaluation | melting temperature (° C.) | melting temperature | gel strength | permeation rate | compatibility | spreadability |
|---|---|---|---|---|---|---|---|---|---|
| Ex. 5 | 10/90 | mineral oil | 12 | 130 | ○ | ○ | ○ | ◉ | ◉ |
| Ex. 6 | | isopropyl myristate | 11 | 105 | ○ | Δ | ○ | ◉ | ◉ |
| Ex. 7 | | triethylhexanoin | 12 | 105 | ○ | ○ | ○ | ◉ | ◉ |
| Ex. 8 | | cyclopentasiloxane/ octyldodecanol 80/20 | 12 | 105 | ○ | ○ | ○ | ◉ | ◉ |
| Comp. Ex. 13 | 50/50 | mineral oil | 4 | 120 | ◉ | X | X | Δ | X |
| Comp. Ex. 14 | | isopropyl myristate | 5 | 100 | ◉ | X | X | ○ | X |
| Comp. Ex. 15 | | triethylhexanoin | 6 | 100 | ◉ | Δ | X | ○ | X |
| Comp. Ex. 16 | | cyclopentasiloxane/ octyldodecanol 80/20 | 6 | 100 | ◉ | Δ | Δ | Δ | X |
| Comp. Ex. 17 | 30/70 | mineral oil | 7 | 125 | ○ | ○ | Δ | ○ | X |
| Comp. Ex. 18 | | isopropyl myristate | 6 | 105 | ○ | X | Δ | ◉ | X |
| Comp. Ex. 19 | | triethylhexanoin | 7 | 105 | ○ | Δ | Δ | ◉ | X |
| Comp. Ex. 20 | | cyclopentasiloxane/ octyldodecanol 80/20 | 7 | 105 | ○ | Δ | ○ | ○ | X |
| Comp. Ex. 21 | 0/100 | mineral oil | 6 | 145 | X | ○ | ○ | X | ○ |
| Comp. Ex. 22 | | isopropyl myristate | 7 | 125 | X | ○ | ○ | X | ◉ |
| Comp. Ex. 23 | | triethylhexanoin | 7 | 125 | X | ○ | ○ | X | ◉ |
| Comp. Ex. 24 | | cyclopentasiloxane/ octyldodecanol 80/20 | 6 | 125 | X | ○ | ○ | X | ○ | ibility and (3) stickiness to the following evaluation criteria by 4 professional panelists. Evaluated by four professional panelists according to the following criteria.

spreadability on the skin (evaluated with 4 points as full mark)
4: very good spreadability
3: good spreadability
2: bad spreadability
1: very bad spreadability compatibility with skin (evaluated with 4 points as full mark)
4: very good compatibility with skin
3: good compatibility with skin
2: bad compatibility with skin
1: very bad compatibility with skin stickiness (evaluated with 4 points as full mark)
4: stickiness not felt at all
3: stickiness felt not much
2: stickiness felt
1: stickiness felt very much Average points of not less than 3.5 is marked with ⊙, not less than 2.5 and less than 3.5 is marked with ○, not less than 1.5 and less than 2.5 is marked with Δ, less than 1.5 is marked m with x.

[Bending Strength]

The bending strength of the obtained chapsticks was measured by rheometer (FUDOH RHEO METER NRM-2010-J-CW). As an adapter, toothed push bar A was used, and the sample table speed was 6 cm/min. The cross section of the chapstick was a circle with diameter 10 mm. The chapstick was extended such that the length from an exclusive container was 20 mm, and the measurement sample was fixed such that the adapter would come into contact with the middle part thereof (10 mm from the end of exclusive container). The bending strength obtained by this measurement was evaluated according to the following criteria.
⊙: 200 g/cm² or more
○: 150 g/cm² or more and less than 200 g/cm²
Δ: 100 g/cm² or more and less than 150 g/cm²
x: less than 100 g/cm²

The components used for the experiment were as follows.

bis(lauroylglutamic acid/lauroylsarcosine)dimer dilinoleate: manufactured by Ajinomoto Co., Inc., "Eldew" DA-209 octyldodecanol: manufactured by Kokyu Alcohol Kogyo Co., Ltd., RISONOL 20SP diisostearyl malate: manufactured by Kokyu Alcohol Kogyo Co., Ltd., HAIMALATE DIS cyclopentasiloxane: TORAY•Dow Corning Corporation, SH245 Fluid lauroylglutamic acid di(phytosteryl/octyldodecyl): manufactured by Ajinomoto Co., Inc., "Eldew" PS-203 dimer dilinoleic acid dimer dilinoleyl bis(behenyl/isostearyl/phytosteryl): manufactured by NIPPON FINE CHEMICAL CO., LTD., PLANDOOL G hydrogenated polyisobutene: manufactured by NOF CORPORATION, parleam 18

From Table 3, it is clear that a chapstick composed of a blend of N-2-ethylhexanoylglutamic acid dibutylamide and N-lauroylglutamic acid dibutylamide, each having a DL form ratio of 10/90, and bis(lauroylglutamic acid/lauroylsarcosine)dimer dilinoleate is further superior in spreadability and compatibility, and free of stickiness. The chapstick of Comparative Example 27 could be prepared only when an oil bath was used at a high temperature of 150° C. or above.

<Preparation of Chapstick (Rod Composition)>

The starting materials shown in the following Table 4 were dissolved by heating in an oil bath at 140° C., and allowed to cool in an exclusive container for 24 hr, and in a room at room temperature 25° C., whereby chapstick was prepared.

The obtained chapsticks showed almost equivalent property to Example 9.

TABLE 3

|  |  | Ex. 9 | Comp. Ex. 25 | Comp. Ex. 26 | Comp. Ex. 27 |
|---|---|---|---|---|---|
| component A | N-2-ethylhexanoyl glutamic acid dibutylamide (DL form ratio 10/90) | 2.0 | | | |
|  | N-lauroyl glutamic acid dibutylamide (DL form ratio 10/90) | 3.0 | | | |
|  | N-2-ethylhexanoyl glutamic acid dibutylamide (DL form ratio 50/50) | | 2.0 | 2.0 | |
|  | N-lauroyl glutamic acid dibutylamide (DL form ratio 50/50) | | 3.0 | 3.0 | |
|  | N-2-ethylhexanoyl glutamic acid dibutylamide (DL form ratio 0/100) | | | | 2.0 |
|  | N-lauroyl glutamic acid dibutylamide (DL form ratio 0/100) | | | | 3.0 |
| component B | octyldodecanol | 20.0 | 20.0 | 20.0 | 20.0 |
|  | diisostearyl malate | 17.0 | 17.0 | 17.0 | 17.0 |
|  | cyclopentasiloxane | 2.0 | 2.0 | 2.0 | 2.0 |
| component C | bis(lauroyl glutamic acid/lauroylsarcosine)dimer dilinoleate | 10.0 | | | |
|  | lauroylglutamic acid di(phytosteryl/octyldodecyl) | 5.0 | 5.0 | 5.0 | 5.0 |
|  | dimer dilinoleic acid dimer dilinoleyl bis(behenyl/isostearyl/phytosteryl) | | | 10.0 | 10.0 |
|  | hydrogenated polyisobutene | balance | balance | balance | balance |
|  | total | 100.0 | 100.0 | 100.0 | 100.0 |
| evaluation | spreadability | ⊙ | x | x | Δ |
|  | compatibility | ⊙ | x | x | x |
|  | stickiness | ⊙ | x | x | x |
|  | bending strength | ⊙ | x | x | ⊙ |

The components used were the same as those in Table 3.

TABLE 4

| | | Ex. 10 | Ex. 11 | Ex. 12 | Ex. 13 | Ex. 14 |
|---|---|---|---|---|---|---|
| component A | N-2-ethylhexanoyl glutamic acid dibutylamide (DL form ratio 20/80) | 2.0 | | | | |
| | N-lauroyl glutamic acid dibutylamide (DL form ratio 20/80) | 3.0 | | | | |
| | N-2-ethylhexanoyl glutamic acid dibutylamide (DL form ratio 15/85) | | 2.0 | | | |
| | N-lauroyl glutamic acid dibutylamide (DL form ratio 15/85) | | 3.0 | | | |
| | N-2-ethylhexanoyl glutamic acid dibutylamide (DL form ratio 13/87) | | | 2.0 | | |
| | N-lauroyl glutamic acid dibutylamide (DL form ratio 13/87) | | | 3.0 | | |
| | N-2-ethylhexanoyl glutamic acid dibutylamide (DL form ratio 7/93) | | | | 2.0 | |
| | N-lauroyl glutamic acid dibutylamide (DL form ratio 7/93) | | | | 3.0 | |
| | N-2-ethylhexanoyl glutamic acid dibutylamide (DL form ratio 5/95) | | | | | 2.0 |
| | N-lauroyl glutamic acid dibutylamide (DL form ratio 5/95) | | | | | 3.0 |
| component B | octyldodecanol | 20.0 | 20.0 | 20.0 | 20.0 | 20.0 |
| | diisostearyl malate | 17.0 | 17.0 | 17.0 | 17.0 | 17.0 |
| | cyclopentasiloxane | 2.0 | 2.0 | 2.0 | 2.0 | 2.0 |
| component C | bis(lauroylglutamic acid/lauroylsarcosine)dimer dilinoleate | 10.0 | 10.0 | 10.0 | 10.0 | 10.0 |
| | lauroyl glutamic acid di(phytosteryl/octyldodecyl) | 5.0 | 5.0 | 5.0 | 5.0 | 5.0 |
| | hydrogenated polyisobutene | balance | balance | balance | balance | balance |
| | total (g) | 100.0 | 100.0 | 100.0 | 100.0 | 100.0 |

<Preparation of Sweating Suppressive Gel Stick>

1)-5) in Table 5 were dissolved at 105° C., cooled to 80° C., the above-mentioned 6) was added, and the mixture was allowed to cool to room temperature, whereby a sweating suppressive gel stick was obtained. The product had sufficient gel strength, was superior in spreadability and compatibility, and free of stickiness.

TABLE 5

| | | |
|---|---|---|
| 1) | N-2-ethylhexanoyl glutamic acid dibutylamide (DL form ratio 10/90) | 2.0 |
| 2) | N-lauroyl glutamic acid dibutylamide (DL form ratio 10/90) | 3.0 |
| 3) | 2-hexyldecanol | 25.0 |
| 4) | C12-15 benzoic acid ester | 11.0 |
| 5) | cyclomethicone D-5 (TORAY Dow Corning Corporation SH245) | 34.0 |
| 6) | Aluminum zirconium trichlorohydrex glycine (Westwood Chemical Corporation Westchlor ZR 30B DM CP-5) | 25.0 |
| | total (g) | 100.0 |

INDUSTRIAL APPLICABILITY

According to the present invention, a gel composition superior in transparency and strength, and superior in compatibility and spreadability when applied to the skin, hair and the like can be prepared without requiring a high temperature of 150° C. or above.

The invention claimed is:

1. A gelling agent, comprising:
at least one compound selected from the group consisting of N-2-ethylhexanoyl glutamic acid dibutylamide and N-lauroyl glutamic acid dibutylamide,
wherein the compound has a DL form ratio (D form/L form (weight/weight)) of 5/95 to 20/80.

2. A gel composition, comprising:
(A) a gelling agent according to claim 1; and
(B) an oily base.

3. The gel composition according to claim 2, wherein (B) said oily base is at least one member selected from the group consisting of a silicone oil, an ester oil, a hydrocarbon, a higher alcohol, a polyvalent alcohol, and a fatty acid.

4. The gel composition according to claim 2, further comprising:
(C) an ester of acyl amino acid and dimer diol and/or an ester of acylamino acid and fatty acid and dimer diol.

5. The gel composition according to claim 3, further comprising:
(C) an ester of acyl amino acid and dimer diol and/or an ester of acylamino acid and fatty acid and dimer diol.

6. The gel composition according to claim 4, wherein (C) said ester of acyl amino acid and dimer diol and/or an ester of acylamino acid and fatty acid and dimer diol is one or more members selected from the group consisting of an ester of lauroyl glutamic acid and dimer diol, an ester of lauroyl sarcosine and dimer diol, and bis(lauroyl glutamic acid/lauroyl sarcosine)dimer dilinoleate.

7. The gel composition according to claim 5, wherein (C) said ester of acyl amino acid and dimer diol and/or an ester of acylamino acid and fatty acid and dimer diol is one or more members selected from the group consisting of an ester of lauroyl glutamic acid and dimer diol, an ester of lauroyl sarcosine and dimer diol, and bis(lauroyl glutamic acid/lauroyl sarcosine)dimer dilinoleate.

8. The gel composition according to claim 4, wherein said (A) is present in an amount of 0.01 to 30 wt %, based on the total weight of the gel composition, said (C) is present in an amount of 0.1 to 60 wt %, based on the total weight of the gel composition, and the total of the amounts of said (B) and said (C) is 30 to 99.99 wt %, based on the total weight of the gel composition.

9. The gel composition according to claim 2, which has a shape of a rod.

10. The gel composition according to claim 2, which is an adiaphoretic cosmetic, chapstick, or rouge.

* * * * *